United States Patent [19]

Priegnitz

[11] Patent Number: 4,540,585
[45] Date of Patent: Sep. 10, 1985

[54] FOOD PRODUCTS CONTAINING α-AMYLASE AND PROCESS

[75] Inventor: Ronald D. Priegnitz, Algonquin, Ill.

[73] Assignee: The Quaker Oats Company, Chicago, Ill.

[21] Appl. No.: 517,878

[22] Filed: Jul. 27, 1983

Related U.S. Application Data

[63] Continuation of Ser. No. 262,252, May 11, 1981, abandoned.

[51] Int. Cl.$^3$ .................. A21D 13/06; A23K 1/00; A23L 3/34
[52] U.S. Cl. .................. 426/28; 426/64; 426/321; 426/549; 426/516; 426/805
[58] Field of Search .................. 426/18, 28, 61, 641, 426/321, 805, 64, 2, 496, 549, 516

[56] References Cited

U.S. PATENT DOCUMENTS

| | | | |
|---|---|---|---|
| 2,615,810 | 10/1952 | Stone | 426/64 |
| 3,202,514 | 8/1965 | Burgess et al. | 426/532 |
| 3,617,300 | 11/1971 | Borochoff et al. | 426/28 |
| 3,745,021 | 7/1973 | Van Middlesworth et al. | 426/646 |
| 3,950,543 | 4/1976 | Buffa et al. | 426/18 |
| 3,968,255 | 7/1976 | Haas et al. | 426/657 |
| 4,190,679 | 2/1980 | Coffee et al. | 426/805 |
| 4,299,848 | 11/1981 | De Stefanis et al. | 426/64 |
| 4,320,151 | 3/1982 | Cole | 426/18 |
| 4,344,969 | 8/1982 | Youngquist et al. | 426/18 |
| 4,376,129 | 3/1983 | Piukovich et al. | 426/635 |
| 4,391,829 | 7/1983 | Spradlin et al. | 426/28 |
| 4,393,085 | 7/1983 | Spradlin et al. | 426/28 |
| 4,418,086 | 11/1983 | Marino et al. | 426/805 |

FOREIGN PATENT DOCUMENTS

1544499  4/1976  United Kingdom .

*Primary Examiner*—Raymond Jones
*Assistant Examiner*—Elizabeth C. Weimar
*Attorney, Agent, or Firm*—Karen E. Ayd; Daniel W. Latham

[57] ABSTRACT

A pet food product containing at least one amylaceous ingredient maintains or improves its soft texture during storage when the enzyme α-amylase is added thereto and processed using heat.

5 Claims, No Drawings

FOOD PRODUCTS CONTAINING α-AMYLASE AND PROCESS

This application is a continuation of application Ser. No. 262,252, filed May 11, 1981, now abandoned.

BACKGROUND OF THE INVENTION

This invention relates to food products and more particularly to food products of an amylaceous character containing heat stable α-amylase which is added in amounts sufficient to maintain or improve the soft texture after a heat treatment.

While it is well recognized that many features contribute to the taste of a food, it is equally well recognized that an important taste feature of a food is its texture, or, the relative softness of the food. A food that feels hard or conversely, extremely soft or mushy may not be acceptable, the desired texture lying generally somewhere in the intermediate range. Foods such as meat or meat substitutes are usually expected to be relatively soft. Some products though initially of a soft texture, such as bread, are known to stale and become hard upon storage. No imagination is needed to realize that with a wide variety of foods, texture or, retaining a soft texture, can be a large problem.

Even though it is possible to manufacture a food product having initially the desired soft texture, staling and the like are factors encountered on storage which can have an adverse effect on texture.

Because such hardness and change in texture is inherently undesirable in most food products, it thus becomes clearly desirable to prevent this change in texture or reduce the texture deterioration in a stored food.

Procedures are known in the prior art for achieving a food having a soft texture by addition of such ingredients as humectants. In some cases, a food which is manufactured with a soft texture has such a low amount of texture deterioration that storage is highly feasible for that food without a substantial loss in texture. Even in these cases, there is some loss of texture which can become detrimental if the storage is overly extended. The components generally used to achieve the desired texture are costly and can have a somewhat adverse effect on palatability.

Besides the use of humectants as taught in U.S. Pat. No. 3,202,514 to Burgess, another way to achieve and maintain a soft texture is through the use of certain emulsifiers which tend to complex with the starch, thereby retarding starch degradation. However emulsifiers only slow down the rate of staling, and do not completely inhibit it.

It has been known in the past to add an amylase enzyme to bakery products such as breads, to achieve a softening of the bread texture. However, in the baking process, the bread dough is cooked at a sufficiently high temperature for a sufficiently long time to assure inactivation of the enzyme during baking. Thus no texturization of the bread can occur after baking, and the bread also will become hard or stale with time.

SUMMARY OF THE INVENTION

Therefore, an object of the subject invention is a food product and a process for preparing a soft food product having a texture which can be maintained during storage.

A still further object of the subject invention is a food product, such as a pet food, having improved texture upon storage while avoiding adverse effects on its palatability.

These and other objects of this invention are accomplished by adding an effective amount of α-amylase containing material to a food product, processing the food product using heat without completely inactivating the α-amylase and then holding such product in storage such that the soft texture is maintained or improved upon storage.

DESCRIPTION OF THE PREFERRED EMBODIMENTS

A food product containing an amylaceous ingredient, such as cereal grains, maintained or improved its texture due to the addition of an effective amount of active α-amylase.

The amount of α-amylase suitable for use in this invention varies substantially depending on the type of food product in which it is to be used, and can be easily determined by a person having ordinary skill in the art. Generally speaking, from a trace to about 5000 SKB units of α-amylase is added for each kilogram of starch in the food being made and is present in the food after processing. More preferably, from about 0.25 SKB units to about 2000 SKB units per kilogram of starch in the product is in the food after processing. Even more preferably, about 0.5 SKB units per kilogram of product to about 1000 SKB units per kilogram of starch in the product may be added to achieve the appropriate levels in the food product after processing. The reference to SKB units is well known in the art as a definition for amylase activity as set forth in Sanstedt, et, al., Cereal Chemistry, Vol. 16, page 712, (1939). A factor to be considered in determining the effective amount of enzyme to be used to achieve a desired texture in a food product is the moisture content of the food product. Unless the food product contains over fifteen percent moisture, only minimal or no texturizing effect will be noted. Based on current observations, it would appear that appreciable enzymatic activity of the α-amylase occurs only at moisture levels above about fifteen percent.

α-Amylase is a well known enzyme, having an IUB number of 3.2.1.1, which defines α-amylase in an internationally accepted manner. It is also known as 1,4-α-D glucan glucanohydrolase. α-Amylase is generally present in all amylaceous materials at low levels and, by previous practices, was generally reduced to a low ineffective concentration or activity level by baking. According to the subject invention, α-amylase is now added to the food product in quantities, that will assure a sufficiently high activity level after processing to maintain or improve the texture of the food product. In this manner texture deterioration in the food product is avoided even after storage.

While not completely understood, it is theorized that within an amylaceous product the active α-amylase present reacts to hydrolyze the starch, thus reducing the amount of long starch chains available for retrogradation, and resulting in a soft texture throughout the entire product. However the starch does not become susceptible to the action of the enzyme until gelatinization of the starch occurs at temperatures destructive to the α-amylase. As a result, the heat processing of a food product generally inactivates the enzyme, allowing a staling process to go forward unless other measures are taken. For instance, the amylase content of a bread dough may affect the texture of the bread initially, however the softness of the bread begins to deteriorate as soon as the baking is completed.

The rate and degree of softening of the food is dependent upon the activity of the enzyme used, the presence and amount of free moisture, enzyme, chloride ion, calcium, the pH and temperature of the product. The α-amylase may be derived from bacterial, fungal, animal, cereal or vegetable sources. Bacterial amylase is preferred for the purpose of this invention because it is readily available, can be readily adapted for use in foods, and is more heat stable. α-Amylase generally is active in a pH range of about 2 to 11 with a moisture content of over 10–15%. The preferred pH range for α-amylase activity is in the 4 to 8 range. Most foods contain sufficient amount of chloride, in the form of salt and calcium to activate the enzyme. If calcium is not present in the food, any suitable source from edible salts may be added, such as calcium phosphate and calcium sulfate.

Effective processing of an amylaceous food product generally depends on temperature and time, and must be sufficient to cook the food and gelatinize the starch, yet insufficient to inactivate the α-amylase. In other words, for an extruded product the temperature and residence time in an extruder must be sufficient to cook the food and gelatinize the starch, yet insufficient to inactivate the α-amylase. Processing temperatures of food containing α-amylase can range up to 150° C. for short periods of time with the effective amounts of the added α-amylase remaining active. However, it is more preferable to operate at process temperatures between 75° C. and 110° C., which is an effective temperature range for achieving most food processing and stabilization. It is critical that the α-amylase not be totally or substantially inactivated by such conditions as overly high temperatures or long retention times during processing.

Generally speaking, the higher the temperature of the extruder, the lower the residence time the food is permitted to be in the extruder. Preferably, from entry into the extruder to exit from the extruder, the time frame may be from 5 seconds to 15 minutes, dependent chiefly on the extruder used and the output rate.

Comparison tests of food with and without α-amylase added show that extruded foods with α-amylase added are at least 5 percent softer and sometimes 10 to 50 percent softer than the extruded foods without α-amylase added, when stored for the same period of time under the same conditions. Thus food products without the α-amylase added, that is, containing only natural levels of the enzyme, experienced a staling or hardening effect, while the food products with the additional α-amylase were at least as soft as the original texture, and sometimes softer as measured by the standard methods used for determining the softness of the food, i.e., the Kramer Shear Press method or alternatively by the Instron method, both known in the art.

While this concept is applicable to any type of food, it is especially applicable to semi-moist foods because a soft and moist texture is of considerable importance in semi-moist human or pet foods. While in the past the desired texture has been accomplished by adding considerable amounts of plasticizers or humectants, these ingredients are now not necessary to provide a soft texture. The presence of the added α-amylase with the other ingredients during processing provides the desired soft texture without added humectants or plasticizers. As stated above, the enzyme is believed to hydrolyze the starch thus reducing the long starch chain available for retrogradation. The resultant product is less apt to stale because most of the starch components not already in the crystalline state are hydrolyzed and cannot retrograde. The hydrolysis of the starch does not take place appreciably until the starch is gelatinized. Of course, if pregelatinized starch sources are used rather than unprocessed starch sources, enzymatic hydrolysis of the starch will take place in the product dough. Thus, by adding the α-amylase and maintaining its activity through a judicious choice of processing parameters with regard to temperature and time as set forth above, the α-amylase can hydrolyze the gelatinized starch in a controlled manner, even during storage. In this fashion, the product cannot only retain its initial soft texture, but can even become softer with the passage of time.

Another advantage in adding α-amylase is an improvement in palatability upon storage. It is theorized that the enzymatic hydrolysis increases the sweetness of the product during storage, since dextrins are formed, in addition to its texture softening action. It is also well known that both humans and pets prefer a soft, moist, and sweet product. The α-amylase produces just such effects on storage.

If, indeed, a pet food is desired to be formed using α-amylase, it must contain a sufficient amount of protein from either an animal source, a cereal source, a vegetable source, or mixtures thereof to provide the protein requirements as set forth by the National Research Council. Also, other ingredients to provide a suitable pet food may be included, as known in the art.

As indicated, the protein source for a pet food product is either a vegetable protein source, a cereal protein source, an animal derived protein source, or a combination thereof. The critical point of the protein source is that it must provide the nutritional and legal requirements for the protein in the product. Generally speaking, the protein content in the pet food must be at least about 5 percent to about 50, and more preferably 10 percent to 40 percent on a dry basis. Protein levels are critical depending on the type of pet food being fed. A dog food protein content is advantageously above 22 percent by weight of the pet food on a dry basis while a cat food protein content is advantageously above 28 percent by weight on a dry basis which are recommendations made by National Research Council for dogs and cats respectively to have a completely nutritional food.

The starch content of the food product of the subject invention may vary from 10% to 60% of the total ingredients. A starch content less than 10% may not provide a significant enough texturizing effect on the food product to be noticeable, while more than 60% starch can result in an excessively soft texture. Such starches will usually originate predominately from cereal grains; however other sources, such as tubers and legumes, may be used.

The subject invention has been found particularly useful in maintaining and enhancing the texture of semi-moist pet foods. A typical semi-moist pet food of about 15 percent to about 40 percent moisture content has about 3 percent to about 65 percent of a protein source, which may comprise meat, vegetable, meat meals or mixtures thereof. A preservative system comprising sugars, edible acids and antimycotic agents may be utilized as described in U.S. Pat. No. 3,202,514. Other additives, such as vitamins, minerals, colorants, flavorants, and salts may be added as desired.

While the invention is now clearly disclosed as to how to make and use the invention, the following Examples are presented to guarantee an understanding of the invention without necessarily limiting the invention. All parts and percentages are by weight unless otherwise specified.

EXAMPLE I

EXPANDED SEMI-MOIST PET FOOD

| Ingredients | (A) (Without) (α-Amylase) | (B) (With) (α-Amylase) |
| --- | --- | --- |
| Meat and Bone Meal | 18.0 pts | 18.0 pts |
| Wheat Flour | 18.0 pts | 18.0 pts |
| Oatmeal | 9.0 pts | 9.0 pts |
| Soy Flour | 9.0 pts | 9.0 pts |
| Propylene Glycol | 5.0 pts | 5.0 pts |
| Ground Yellow Corn | 5.0 pts | 5.0 pts |
| Animal Fat | 4.5 pts | 4.5 pts |
| Oat Flour | 3.0 pts | 3.0 pts |
| Phosphoric Acid | 1.0 pts | 1.0 pts |
| Potassium Sorbate | 0.1 pts | 0.1 pts |
| Vitamins, Minerals, Color | 1.4 pts | 1.4 pts |
| α-Amylase* | — | 30 SKB Units/ kg. starch |
| Water | 26.0 pts | 26.0 pts |
|  | 100.0 pts | 100.0 pts |

*Available from Miles Laboratories as HT-1000

The above products were processed on a Bonnot extruder at 225° F. The resulting products each had bulk densities of 31 lbs/ft.$^3$ and moisture contents of 30%. Both samples were identical in appearance and texture when first made. However, after 8 months of storage at both 73° F. and 100° F., the product containing the α-amylase enzyme was considerably softer. Both stored products were measured for softness on the Kramer Shear Press with the following results:

| Product | SAMPLE Age | Maximum Peak Height at 73° F. Storage | Maximum Peak Height at 100° F. Storage |
| --- | --- | --- | --- |
| A (no enzyme) | 8 months | 89.7 | 94.6 |
| B (with enzyme) | 8 months | 58.2 | 51.5 |

The data from the Kramer Shear Press readings confirmed the observed softer texture of the product containing α-amylase. Also, the higher storage temperature seemed to increase the amount of softening by the enzyme, which was apparent both by observation and by the Kramer Shear Press readings.

EXAMPLE II

EXPANDED SEMI-MOIST PET FOOD

A formulation similar to that in Example I was used to test the texture softening action of Miles Taka-Therm ® α-amylase, an amylase having a different activity level than Miles HT-1000. As in Example I, the only difference was that one contained 100 SKB units/kg-starch Miles Taka-Therm ® α-amylase (D) and the other (C) did not.

Both products were processed at 230° F. in an extruder, and had finished product moisture contents of 30%, being expanded to a density of 32 lbs/ft.$^3$. No differences in product texture were observed initially, but after 3½ months of ambient storage, the product containing the α-amylase was considerably softer. The following measurements were made on the stored products using a shear cell on an Instron Universal Testing Machine, Model II:

| Shear Cell Conditions | Sample |
| --- | --- |
| Sample Size: 40 gm | C, no enzyme |
| Stroke Length: 6 gm | D, α-amylase |
| Stroke Speed: 10 cm./min. |  |
| Full Scale: 50 Kg. full scale |  |

| Product Measurements | |
| --- | --- |
| Age | Average Peak Height |
| C, 3½ months | 410.5 cm |
| D, 3½ months | 263.5 cm |

As can be seen, the Instron measurements confirmed the improved softness observed in the stored sample containing α-amylase enzyme.

EXAMPLE III

NON-EXPANDED SEMI-MOIST PET FOOD

| Ingredients | E Without α-Amylase | F With σ-Amylase |
| --- | --- | --- |
| Meat By-Products | 25.0 pts | 25.0 pts |
| Wheat Flour | 25.0 pts | 25.0 pts |
| Soybean Flour | 19.0 pts | 19.0 pts |
| Corn Syrup | 6.0 pts | 6.0 pts |
| Propylene Glycol | 5.0 pts | 5.0 pts |
| Corn Flour | 4.0 pts | 4.0 pts |
| Phosphoric Acid | 1.0 pts | 1.0 pts |
| Potassium Sorbate | 0.1 pts | 0.1 pts |
| Vitamins, Minerals, Color, etc. | 5.9 pts | 5.9 pts |
| α-Amylase* | — | 600 SKB Units/ kg. Starch |
| Water | 9.0 pts | 9.0 pts |
|  | 100.0 pts | 100.0 pts |

*Available from Miles Laboratories as HT-1000

The above products were processed on a Bonnot extruder at 190° F. The products were made in a strand form at a finished product moisture content of 30%, and were tested for palatability initially and after 9 months of ambient storage. After nine months the observed softness of the product F (with α-amylase) was greater than product E (without α-amylase). A standard 2 bowl preference method was used to obtain the following results on palatability:

| Product | % Consumption | Level of Statistical Significance |
| --- | --- | --- |
| | Initial 2-Pan Test | |
| E, (without α-amylase) | 46 | (Not Significant) |
| F, (with α-amylase) | 54 | |
| | Nine Month Storage 2-Pan Test | |
| E, (without α-amylase) | 36 | 99% (Highly Significant) |
| F, (with α-amylase) | 64 | |

According to the above data there was no initial significant difference in the palatability of the products with or without α-amylase. However, after nine months of storage, not only was the product with enzyme noticably softer, but it was significantly more palatable than the same product without the enzyme.

EXAMPLE IV

The procedure of Example III is applied to the following formulation:

| Ingredients | Formula |
| --- | --- |
| Granola Mix (Oat flakes, Wheat flakes, Nuts, Honey, etc.) | 45 pts |
| Sucrose | 10 pts |
| Glycerol | 10 pts |
| Shortening | 5 pts |
| Vitamins, Minerals, Flavor, Phosphoric Acid, and Potassium Sorbate | 2 pts |
| α-Amylase | 20. SKB Units/kg. Starch |
| Water | 28 pts |
| | 100. |

The product of Example 4 results in a granola snack bar which maintains a soft product texture over an extended shelflife without becoming hard or crumbly in texture. The α-amylase maintains the desired texture, but does not hydrolyze to the point where the product becomes too soft.

The above examples show that α-amylase is useful as a texturizing agent, not only preventing the degradation of a soft texture of a food product but even contributing to the improvement of the texture of the food product on storage. As stated and as demonstrated in the examples, the subject invention applies to all food products having amylaceous ingredients, regardless of whether the food product is for humans or for pets.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

I claim:

1. In a soft, semi-moist pet food product consisting of soft, cohesive, extrusion cooked particles having 10–60% starch, 22–50% protein, 5–35% water soluble solutes, and 15–40% moisture; the improvement comprising:
   an enzyme in the pet food product consisting essentially of alpha-amylase, wherein the alpha-amylase is in an active condition and wherein the active condition alpha-amylase is in the pet food in sufficient quantity to maintain the soft texture of the pet food product during subsequent storage.

2. The improved pet food product according to claim 1 wherein the improved pet food product has a pH in the range 2–10.

3. The improved pet food product according to claim 1 wherein the alpha-amylase is present in the improved pet food product in an amount from a trace to 5,000 SKB units of alpha-amylase for each kilogram of starch.

4. In a method for makig a soft, semi-moist pet food by the steps of admixing a dough having at least one amylaceous ingredient, at least one proteinaceous ingredient selected from animal, vegetable or cereal sources, sufficient water to provide a moisture content in the pet food product in the range 15–40% and at least one water soluble solute selected from sugars and polyols; and extrusion cooking the dough at a temperature in the range 75°–110° C. inclusive for a time period in the range 15 seconds to 5 minutes inclusive, the improvement comprising:
   (a) adding to the dough an enzyme ingredient consisting essentially of a heat-stable alpha-amylase enzyme;
   (b) extrusion cooking the dough containing alpha-amylase at a temperature and for a time period sufficiently mild that at least some alpha-amylase remains active in the extrusion cooked pet food product; and
   (c) storing the pet food product containing the active alpha-amylase.

5. The improved process according to claim 4 wherein from a trace of 5000 SKB units of alpha-amylase for each kilogram of amylaceous ingredient is added to the dough.

* * * * *